United States Patent [19]

Gaster

[11] Patent Number: 5,700,818
[45] Date of Patent: Dec. 23, 1997

[54] DIHYDROBENZOFURANYL-BIPHENYL CARBOXAMIDES HAVING 5HT$_{1D}$ ANTAGONISTIC ACTIVITY

[75] Inventor: Laramie Mary Gaster, Bishops Stortford, United Kingdom

[73] Assignee: SmithKline Beecham p.l.c., Brentford, England

[21] Appl. No.: 663,290

[22] PCT Filed: Dec. 16, 1994

[86] PCT No.: PCT/EP94/04180

§ 371 Date: Jun. 20, 1996

§ 102(e) Date: Jun. 20, 1996

[87] PCT Pub. No.: WO95/17401

PCT Pub. Date: Jun. 29, 1995

[30] Foreign Application Priority Data

Dec. 21, 1993 [GB] United Kingdom ............... 9326008

[51] Int. Cl.$^6$ .................................................. A61K 31/41
[52] U.S. Cl. ............................ 514/364; 546/250; 548/131
[58] Field of Search .......................... 548/131; 546/250; 514/364

[56] References Cited

FOREIGN PATENT DOCUMENTS

| 0 533 266 | 3/1993 | European Pat. Off. . |
| 0 533 268 | 3/1993 | European Pat. Off. . |
| 2 276 164 | 9/1994 | United Kingdom . |

*Primary Examiner*—Mukund J. Shah
*Assistant Examiner*—Michael Bucknum
*Attorney, Agent, or Firm*—Wayne J. Dustman; Charles M. Kinzig; Edward T. Lentz

[57] ABSTRACT

This invention discloses dyhydrobenzofuranyl-biphenyl carboxamides having 5HT$_{1D}$ antagonistic activity.

9 Claims, No Drawings

DIHYDROBENZOFURANYL-BIPHENYL CARBOXAMIDES HAVING 5HT$_{1D}$ ANTAGONISTIC ACTIVITY

The present invention relates to novel amide derivatives, processes for their preparation, and pharmaceutical compositions containing them.

EPA 0 533 266/7/8 disclose a series of benzanilide derivatives which are said to possess 5HT$_{1D}$ receptor antagonist activity. These compounds are said to be of use in the treatment of various CNS disorders.

A structurally distinct class of compounds have now been discovered and have been found to exhibit 5HT$_{1D}$ antagonist activity. In a first aspect, the present invention therefore provides a compound of formula (I) or a salt thereof:

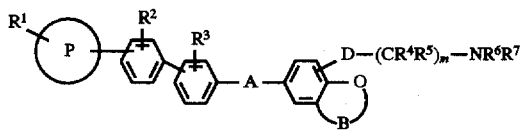

in which
- P is a 5 to 7-membered heterocyclic ring containing 1 to 3 heteroatoms selected from oxygen, nitrogen or sulphur;
- $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^8$, $CONR^9R^{10}$, $NR^9R^{10}$ where $R^8$, $R^9$ and $R^{10}$ are independently hydrogen or $C_{1-6}$alkyl;
- $R^4$ and $R^5$ are independently hydrogen or $C_{1-6}$alkyl;
- $R^6$ and $R^7$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur;
- A is CONH or HNCO;
- B is —$(CR^{11}R^{12})_p$— or —$O(CR^{11}R^{12})_q$— where $R^{11}$ and $R^{12}$ are independently hydrogen or $C_{1-6}$alkyl and p is 2 or 3 and q is 1, 2 or 3;
- m is 1 to 4; and
- D is oxygen, $S(O)_n$ where n is 0, 1 or 2, or D is $NR^{10}$ where $R^{10}$ is hydrogen or $C_{1-6}$alkyl, or D is $CR^4$=$CR^5$ or $CR^4R^5$ where $R^4$ and $R^5$ are independently hydrogen or $C_{1-6}$alkyl.

$C_{1-6}$alkyl groups, whether alone or as part of another group, may be straight chain or branched.

Suitably P is a 5 to 7-membered heterocyclic ring containing 1 to 3 heteroatoms selected from oxygen, nitrogen or sulphur. Examples of suitable heterocyclic rings include pyridyl, thienyl, furyl, pyrrolyl, triazolyl, diazolyl, imidazolyl, oxadiazolyl, isothiazolyl, isoxazolyl, thiadiazolyl, pyridyl, pyrimidyl and pyrazinyl. The heterocyclic rings can be linked to the remainder of the molecule via a carbon atom or, when present, a nitrogen atom. Preferably P is oxadiazolyl.

Suitably $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^8$, $CONR^9R^{10,}$ $NR^9R^{10}$ where $R^8$, $R^9$ and $R^{10}$ are independently hydrogen or $C_{1-6}$alkyl. Preferably $R^1$ and $R^2$ are $C_{1-6}$alkyl, in particular methyl. Preferably $R^3$ is hydrogen.

Suitably $R^4$ and $R^5$ are independently hydrogen or $C_{1-6}$alkyl. Preferably $R^4$ and $R^5$ are both hydrogen.

Suitably $R^6$ and $R^7$ are independently hydrogen, $C_{1-6}$alkyl, aralkyl, or together with the nitrogen atom to which they are attached form an optionally substituted 5- to 7-membered heterocyclic ring containing one or two heteroatoms selected from oxygen, nitrogen or sulphur. Examples of $R^6$ and $R^7$ heterocyclic rings include morpholine, piperazine and piperidine. Examples of $R^6$ and $R^7$ aralkyl groups include benzyl. Optional substituents for such rings include $C_{1-6}$alkyl. Preferably $R^6$ and $R^7$ are both $C_{1-6}$alkyl, in particular methyl.

Suitably A is CONH or NHCO, preferably A is CONH.

Suitably B is —$(CR^{11}R^{12})_p$— or —$O(CR^{11}R^{12})_q$— where $R^{11}$ and $R^{12}$ are independently hydrogen or $C_{1-6}$alkyl and p is 2 or 3 and q is 1, 2 or 3. Preferably B is —$(CRuR^{12})_p$— where $R^{11}$ and $R^{12}$ are both hydrogen and p is 2, that is to say, B forms part of a dihydrobenzofuran ring.

Suitably D is oxygen, $S(O)_n$ where n is 0, 1 or 2, or D is $NR^{10}$ where $R^{10}$ is hydrogen or $C_{1-6}$alkyl or D is $CR^4$=$CR^5$ or $CR^4R^5$ where $R^4$ and $R^5$ are independently hydrogen or $C_{1-6}$alkyl. Preferably D is oxygen, NH or $CH_2$.

Suitably m is 1 to 4, preferably m is 2.

The group —$D(CR^4R^5)_m NR^6R^7$ can be attached to the phenyl ring at any suitable position. Preferably the group —$D(CR^4R^5)_m NR^6R^7$ is meta to the amide linkage. The groups $R^1$, $R^2$ and $R^3$ can also be attached at any suitable position.

Particularly preferred compounds of the invention include:
- N-[7-[(2-dimethylaminoethyl)amino]-2,3-dihydrobenzofuran-5-yl]-2'-methyl-4'-(5-methyl-1,2,4-oxadiazol-3-yl)biphenyl-4-carboxamide,
- N-[7-(2-dimethylamino) ethoxy2,3-dihydrobenzofuran5-yl]-2'-methyl-4'-(5-methyl-1,2,4-oxadiazol-3-yl)biphenyl-4-carboxamide,
- N-[7-(3-Dimethylaminopropyl)-2,3-dihydrobenzofuran-5-yl]-2'-methyl-4'-(5-methyl-1,2,4-oxadiazol-3-yl) biphenyl-4-caboxamide, or pharmaceutically acceptable salts thereof.

Preferred salts of the compounds of formula (I) are pharmaceutically acceptable salts. These include acid addition salts such as hydrochlorides, hydrobromides, phosphates, acetates, fumarates, maleates, tartrates, citrates, oxalates, methanesulphonates and p-toluenesulphonates.

Certain compounds of formula (I) are capable of existing in stereoisomeric forms. It will be understood that the invention encompasses all geometric and optical isomers of the compounds of formula (I) and the mixtures thereof including racemates. Tautomers and mixtures thereof also form an aspect of the invention.

In a further aspect the present invention provides a process for the preparation of a compound of formula (I) which comprises.

(a) reaction of a compound of formula (II):

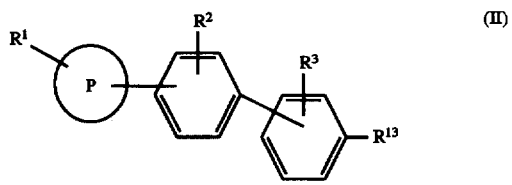

with a compound of formula (III):

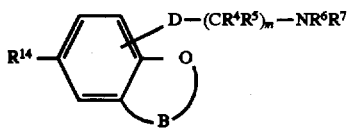

wherein B, D, m, P, R$^1$, R$^2$, R$^3$, R$^4$, R$^5$, R$^6$ and R$^7$ are as defined in formula (I) and R$^{13}$ and R$^{14}$ contain the appropriate functional group(s) necessary to form the A moiety; and optionally thereafter in any order:

converting a compound of formula (I) into another compound of formula (I)

forming a pharmaceutically acceptable salt.

Suitably one of R$^{13}$ or R$^{14}$ is an activated carboxylic acid derivative, such as an acyl halide or acid anhydride, and the other is an amine group. Activated compounds of formulae (II) or (III) can also be prepared by reaction of the corresponding carboxylic acid with a coupling reagent such as carbonyldiimidazole, dicyclohexylcarbodiimide or diphenylphosphorylazole. Preferably R$^{13}$ or R$^{14}$ is a group COL where L is halo, particularly chloro.

Compounds of formulae (II) and (III) are typically reacted together in an inert organic solvent such as DMF, THF or dichloromethane at ambient or elevated temperature in the presence of a base such as an alkali metal hydroxide, triethylamine or pyridine.

Intermediate compounds of formula (II) can be prepared using standard procedures such as those outlined in EPA 533266/7/8. Intermediate compounds of formula (III) can be prepared using routine chemistry. Certain intermediate compounds of formulae (II) and (III) are novel and form a further aspect of the invention.

It will be appreciated to those skilled in the art that it may be necessary to protect certain reactive substituents during some of the above procedures. Standard protection and deprotection techniques can be used. For example, primary amines can be protected as phthalimide, benzyl, benzyloxycarbonyl or trityl derivatives. These groups can be removed by conventional procedures well known in the art.

Carboxylic acid groups can be protected as esters. Aldehyde or ketone groups can be protected as acetals, ketals, thioacetals or thioketals. Deprotection is achieved using standard conditions.

Certain compounds of formula (I) can be converted into further compounds of formula (I) using standard processes. For example compounds in which R$^6$ and R$^7$ are both hydrogen or one of R$^6$ or R$^7$ is hydrogen and the other is C$_{1-6}$alkyl can be convened to compounds in which R$^6$ and R$^7$ are both C$_{1-6}$alkyl using standard alkylation techniques.

5HT$_{1D}$ Antagonists, and in particular the compounds of the present invention, are expected to be of use in the treatment of CNS disorders such as mood disorders, including depression, seasonal effective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviours, including anorexia nervosa and bulimia nervosa. Other CNS disorders include Parkinson's disease, dementia in Parkinson's disease, neuroleptic-induced Parkinsonism and tardive dyskinesias, as well as other psychiatric disorders.

5HT$_{1D}$ Antagonists, and in particular compounds of the present invention, may also be of use in the treatment of endocrine disorders such as hyperprolactinaemia, in the treatment of vasospasm (particularly in the cerebral vasculature) and hypertension, as well as disorders in the gastrointestinal tract where changes in motility and secretion are involved. They may also be of use in the treatment of sexual dysfunction.

Therefore, the present invention, provides a compound of general formula (I) or a physiologically acceptable salt or solvate thereof for use in therapy.

The present invention also provides a compound of general formula (I) or a physiologically acceptable salt or solvate thereof for use in the treatment of the aforementioned disorders.

In another aspect the invention provides the use of a compound of general formula (I) or a pharmaceutically acceptable salt or solvate thereof for the manufacture of a medicament for the treatment of the aforementioned disorders.

In a further aspect the invention provides a method of treating the aforementioned disorders which comprises administering an effective amount to a patient in need of such treatment of a compound of general formula (I) or a pharmaceutically acceptable salt or solvate thereof.

In particular the invention provides a compound of general formula (I) or a physiologically acceptable salt or solvate thereof for use in the treatment or prophylaxis of depression.

It will be appreciated by those skilled in the an that the compounds according to the invention may advantageously be used in conjunction with one or more other therapeutic agents, for instance, different antidepressant agents.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Examples illustrate the preparation of compounds of the invention.

DESCRIPTION 1

2,3-dihydrobenzofuran-7-carboxylic acid (D1)

Following the procedure outlined in EP-A-307172, Example 15, 2,3-dihydrobenzofuran (10.73 g) was converted to the title compound (D1) (6 g, 41%)

$^1$H NMR (250 MHz CDCl$_3$) δ(ppm): 8.76 (brs, 1H), 7.82 (d, 1H), 7.42 (d, 1H), 6.95 (t, 1H) 4.8 (t, 2H), 3.3 (t, 2H)

DESCRIPTION 2

7-(trifluoroacetylamino)-2,3-dihydrobenzofuran (D2)

2,3-dihydrobenzofuran-7-carboxylic acid (D1) (1.42 g) was dissolved in a mixture of trifluoroacetic acid (50 ml) and trifluoroacetic anhydride (10 ml). After stirring at room temperature for 1.5 h, the mixture was cooled to 0° C. and treated portionwise with sodium azide (788 mg, 1.4 eq.), then stirred at room temperature for 2 days under argon. The mixture was evaporated under reduced pressure, and the residue partitioned between CHCl$_3$ and water. The organic phase was washed with K$_2$CO$_3$ (aq), dried (Na$_2$SO$_4$) and the solvent evaporated under reduced pressure, to give the title compound (1.64 g, 82%) as an off-white crystalline material.

$^1$H NMR (250 MHz CDCl$_3$) δ(ppm): 7.85–8.2 (m, 2H), 7.05 (d, 1H), 6.89 (t, 1H), 4.65 (t, 2H), 3.28 (t, 2H)

DESCRIPTION 3

7-amino-2,3-dihydrobenzofuran (D3)

A solution of 7-(trifluoroacetylamino)-2,3-dihydrobenzofuran (D2) (1.6 g) in methanol (30 ml) and 10% NaOH (3 ml) was heated to reflux for 24h. The mixture was evaporated under reduced pressure and partitioned between ethyl acetate and water. The organic phase was dried (Na$_2$SO$_4$) and the solvent evaporated under reduced pressure to give the title compound (900 mg, 96%) as a pale orange oil, which crystallised on standing.

$^1$H NMR (200 MHz CDCl$_3$) δ(ppm): 6.44–6.75 (m, 3H), 4.57 (t, 2H), 3.55 (br s, 2H), 3.2 (t, 2H)

DESCRIPTION 4

7-amino-5-nitro-2,3-dihydrobenzofuran (D4)

Potassium nitrate (8.6 g) was added portionwise over ½ h to a solution of 7-amino-2,3-dihydrobenzofuran (D3) (10 g) in concentrated sulphuric acid (75 ml) at 5°–10° C. The resulting solution was stirred for a further 2 h, then added to ice, basified with 40% NaOH, and extracted into ethyl acetate. The organic phase was dried (Na$_2$SO$_4$) and the solvent evaporated under reduced pressure to give the title compound (10.1 g, 76%) as a red/brown foam.

$^1$H NMR (250 MHz, CDCl$_3$) δ(ppm): 7.59 (s, 1H), 7.49 (s, 1H), 4.72 (t, 2H), 3.81 (br s, 2H), 3.26 (t, 2H)

DESCRIPTION 5

7-(2-dimethylaminoethyl)amino-5-nitro-2,3-dihydrobenzofuran (D5)

A solution of 7-amino-5-nitro-2,3-dihydrobenzofuran (D4) (2 g) in ethanol (60 ml) was treated with 2-dimethylaminoethyl chloride hydrochloride (3.36 g) and excess sodium carbonate (6 g), and heated at reflux for 4 days under argon. The solvent was evaporated under reduced pressure, and the residue partitioned between water and chloroform. The organic phase was dried (Na$_2$SO$_4$) and evaporated under reduced pressure to leave an oil which was chromatographed on silica, eluting with methanol and chloroform to give the title compound as a viscous red oil (416 mg, 15%)

$^1$H NMR (200 MHz, CDCl$_3$) δ(ppm): 7.55 (s, 1H), 7.35 (s, 1H), 4.73 (t, 2H), 4.5 (br s, 1H), 3.35–3.15 (m, 4H), 2.6 (t, 2H), 2.26 (s, 6H)

DESCRIPTION 6

(5-nitro-2,3-dihydrobenzofuran-7-yl)-(2-dimethylaminoethyl)carbamic acid tert-butyl ester (D6)

A solution of 7-(2-dimethylaminoethyl)amino-5-nitro-2,3-dihydrobenzofuran (D5) (416 mg) in dichloromethane (25 ml) was treated with di-tert-butyldicarbonate (433 mg) and triethylamine (0.25 ml), and stirred under argon at room temperature for 24h. The mixture was washed with water, dried (Na$_2$SO$_4$), then the solvent evaporated under reduced pressure to leave the title compound (405 mg, 70%).

$^1$H NMR (200 MHz, CDCl$_3$) δ(ppm): 8.0 (s, 1H), 7.91 (s, 1H), 4.7 (t, 2H), 3.6 (t, 2H), 3.29 (t, 2H), 2.36 (t, 2H), 2.15 (s, 6H), 1.35 (br s, 9H).

DESCRIPTION 7

(5-amino-2,3-dihydrobenzofuran-7-yl)-(2-dimethylaminoethyl) carbamic acid tert-butyl ester (D7)

A solution of 5-nitro-2,3-dihydrobenzofuran-7-yl)-(2-dimethylaminoethyl)carbamic acid tert-butyl ester (D6) (387 mg) in ethanol (50 ml) was hydrogenated over 10% palladium on charcoal for 2 h at atmospheric pressure and room temperature. The catalyst was removed by filtration and the flitrate evaporated under reduced pressure to give the title compound as a brown oil (260 mg, 73%).

$^1$H NMR (200 MHz, CDCl$_3$) δ(ppm): 6.54–6.21 (m, 2H), 4.51 (t, 2H), 3.69 (t, 2H), 3.39–2.99 (m, 4H), 2.5 (t, 2H), 2.28 (s, 6H), 1.44 (br s, 9H)

DESCRIPTION 8

7-acetyl-2,3-dihydrobenzofuran (D8)

To a cooled suspension of 2,3-dihydrobenzofuran-7-carboxylic acid (D1) (2 g) in dry diethyl ether (100 ml) was added dropwise under argon, methyllithium (16.2 ml of a 1.5M solution in diethyl ether). The mixture was stirred at room temperature for 18 h, added to 5N hydrochloric acid (50 ml) and extracted into ethyl acetate. The organic phase was washed with potassium carbonate, then water and dried ($Na_2SO_4$). The solvent was evaporated under reduced pressure to leave the title compound as a plate lemon solid (1.5 g, 76%)

$^1$H NMR (200 MHz, $CDCl_3$) δ(ppm): 7.69 (d, 1H), 7.35 (d, 1H), 6.89 (t, 1H), 4.7 (t, 2H), 3.25 (t, 2H), 2.61 (s, 3H).

DESCRIPTION 9

7-acetyl-5-nitro-2,3-dihydrobenzofuran (D9)

Using the method outlined in description 4,7-acetyl-2,3-dihydrobenzofuran (D8) (500 mg) was converted to the title compound as a cream powder (516 mg, 81%)

$^1$H NMR (250 MHz, $CDCl_3$) δ(ppm): 8.65 (s, 1H), 8.2 (s, 1H), 4.91 (t, 2H), 3.36 (t, 2H), 2.65 (s, 3H).

DESCRIPTION 10

7-hydroxy-5-nitro-2,3-dihydrobenzofuran (D10)

A solution of 7-acetyl-5-nitro-2,3-dihydrobenzofuran (D9) (500 mg) in chloroform (3 ml) was added to m-chloroperoxybenzoic acid (83 mg) in chloroform (8 ml) containing a catalytic quantity of p-toluenesulphonic acid. A further quantity (83 mg) of the peroxy acid was added after 24 h and a further 400 mg after another 24 h. After stirring at room temperature for 3 days under argon, the reaction mixture was washed with sodium bicarbonate solution, dried ($Na_2SO_4$) and the solvent evaporated under reduced pressure, to give the acetoxy intermediate. This was dissolved in ethanol (50 ml) containing 40% sodium hydroxide (5 ml) and stirred for 30 minutes at room temperature. The mixture was acidified with 5N hydrochloric acid, the solvents were evaporated under reduced pressure, and the residue partitioned between water and chloroform. The organic phase was dried ($Na_2SO_4$) and the solvent evaporated under reduced pressure. The residue was chromatographed on silica eluting with 60°–80° Petrol-ether and ethyl acetate to give the title compound (294 mg, 67%).

$^1$H NMR (200 MHz, $CDCl_3$) δ(ppm): 7.8–7.67 (m, 2H), 5.59 (br s, 1H), 4.8 (t, 2H), 3.32 (t, 2H),

DESCRIPTION 11

7-(2-dimethylamino)ethoxy-5-nitro-2,3-dihydrobenzofuran (D11)

A solution of 7-hydroxy-5-nitro-2,3-dihydrobenzofuran (D 10) (280 mg) in dimethoxyethane (20 ml) was treated with 2-dimethylaminoethyl chloride hydrochloride (488 mg) and an excess of potassium carbonate (3 g), and heated to reflux under argon for 18 h. The solvent was evaporated under reduced pressure and the residue partitioned between water and ethyl acetate. The organic phase was dried ($Na_2SO_4$) and the solvent evaporated under reduced pressure to give a yellow oil. This was dissolved in 5N hydrochloric acid and washed with ethyl acetate. The acidic phase was basified with potassium carbonate and extracted into ethyl acetate. The organic phase was washed with water, and dried ($Na_2SO_4$). The solvent was evaporated under reduced pressure to leave the title compound as a yellow crystalline material. (284 mg, 73%).

$^1$H NMR (250 MHz, $CDCl_3$) δ(ppm): 7.8 (s, 1H), 7.71 (s, 1H), 4.8 (t, 2H), 4.2 (t, 2H), 3.31 (t, 2H), 2.8 (t, 2H), 2.36 (s, 6H).

DESCRIPTION 12

5-amino-7-(2-dimethylamino)ethoxy-2,3-dihydrobenzofuran (D12)

Using the method outlined in description 7, 7-(2-dimethylamino)ethoxy-5-nitro-2,3-dihydrobenzofuran (D 11) (274 mg) was converted to the title compound (227 mg, 94%)

$^1$H NMR (200 MHz, $CDCl_3$) δ(ppm): 6.25 (s, 1H), 6.17 (s, 1H), 4.51 (t, 2H), 4.19 (t, 2H), 3.95 (br s, 2H), 3.12 (t, 2H), 2.89 (t, 2H), 2.44 (s, 6H)

DESCRIPTION 13

3-Dimethylamino-1-(5-nitro-2,3-dihydrobenzofuran-7-yl)propene-1-one (D13)

7-Acetyl-5-nitro-2,3-dihydrobenzofuran (D9) (500 mg) was stirred and heated to 80° C. for 1 h with tert-butoxy-bis (dimethylamino) methane (1.08 ml), then the mixture was cooled and partitioned between $Na_2CO_3$ and ethyl acetate. The organic phase was dried ($Na_2SO_4$) and the solvent evaporated under reduced pressure to leave the title compound (0.5 g, 80%).

$^1$H NMR (200 MHz, $CDCl_3$) δ(ppm): 8.65 (s, 1H), 8.1 (s, 1H), 7.85 (d, 1H), 5.88 (d, 1H), 4.82 (t, 2H), 3.3 (t, 2H), 3.14 (br s, 3H), 2.94 (br s, 3H).

DESCRIPTION 14

1-(5-Amino-2,3-dihydrobenzofuran-7-yl)-3-dimethylaminopropene-1-one (D14)

Following the procedure outlined in Description 7, 3-dimethylamino-1-(5-nitro-2,3-dihydrobenzofuran-7-yl) propene-1-one (D13) (500 mg) was converted to the title compound (402 mg, 91%).

$^1$H NMR (200 MHz, $CDCl_3$) δ(ppm): 7.8 (d, 1H), 7.08 (s, 1H), 6.69 (s, 1H), 6.01 (d, 1H), 4.58 (t, 2H), 3.41 (br s, 2H), 3.22–2.72 (m, 8H)

DESCRIPTION 15

1-(5-Amino-2,3-dihydrobenzofuran-7-yl)-3-dimethylaminopropan-1-one (D15)

A solution of 1-(5-amino-2,3-dihydrobenzofuran-7-yl)-3-dimethylamino- propene-1-one (D14) (400 mg) in dry tetrahydrofuran (9 ml) was added to a stirred suspension of lithium aluminium hydride (46 mg) in dry tetrahydrofuran (9 ml) at 0° C. under argon. The mixture was stirred at this temperature for ¼ h then treated sequentially with water (0.046 ml), 10% NaOH (0.068 ml) and water (0.12 ml). After a further ¼ h stirring at room temperature the mixture was filtered through kieselguhr, and washed with dry tetrahydrofuran, and the solvent was evaporated under reduced pressure to give the title compound as a yellow/orange solid (352 mg, 87%).

$^1$H NMR (250 MHz, $CDCl_3$) δ(ppm): 7.0 (s, 1 H), 6.8 (s, 1 H), 4.61 (t, 2H), 3.47 (br s, 2H), 3.21–3.1 (m, 4H), 2.71 (t, 2H), 2.28 (s, 6H)

DESCRIPTION 16

1-(5-Amino-2,3-dihydrobenzofuran-7-yl)-3-dimethylaminopropan-1-ol (D16)

A solution of 1-(5-amino-2,3-dihydrobenzofuran-7-yl)-3-dimethylaminopropan-1-one (D15) (2.5 g) in ethanol (200 ml) was treated with sodium borohydride (1.22 g) and stirred for 4 h at room temperature. The solvent was evaporated under reduced pressure, and the residue partitioned between water and dichloromethane. The organic phase was dried ($Na_2SO_4$) and the solvent evaporated under reduced pressure to give the title compound as an orange/red solid (2.12 g, 84%).

$^1$H NMR (250 MHz, $CDCl_3$) δ(ppm): 6.7 (s, 1H), 6.5 (s, 1H), 5.04–4.95 (m, 1H), 4.56–4.41 (m, 2H), 3.42 (br s, 2H), 3.1 (t, 2H), 2.67–2.41 (m, 2H), 2.29 (s, 6H), 1.91–1.72 (m, 2H).

DESCRIPTION 17

7-(3-Dimethylaminopropenyl)-2,3-dihydrobenzofuran-5-ylamine (D17)

A solution of 1-(5-amino-2,3-dihydrobenzofuran-7-yl)-3-dimethylaminopropan-1-ol (D 16) (2.12 g) in trifluoroacetic acid (60 ml) was refluxed for 10h, cooled and the solvent evaporated under reduced pressure. The residue was partitioned between 10% $Na_2CO_3$ and ethyl acetate, the organic phase was dried ($Na_2SO_4$) and the solvent evaporated under reduced pressure, to give the title compound as an orange foam (2.07 g, quantitative).

$^1$H NMR (200 MHz, $CDCl_3$) δ(ppm): 6.7–6.3 (m, 4H), 4.56 (t, 2H), 3.7 (d, 2H), 3.15 (t, 2H), 2.72 (s, 6H)

DESCRIPTION 18

7-(3-Dimethylaminopropyl)-2,3-dihydrobenzofuran-5-ylamine (D18)

Following the procedure outlined in Description 7, 7-(3-dimethylaminopropenyl)-2,3-dihydrobenzofuran-5-ylamine (D17) (970 mg) was converted to the title compound (793 mg, 81%).

$^1$H NMR (250 MHz, $CDCl_3$) δ(ppm): 6.46 (s, 1H), 6.32 (s, 1H), 4.49 (t, 2H), 3:3 (br s, 2H), 3.11 (t, 2H), 2.58–2.41 (m, 4H), 2.35 (s, 6H), 1.91–1.8 (m, 2H).

EXAMPLE 1

N-[7-[(2-dimethylaminoethyl)amino]-2,3-dihydrobenzofuran-5-yl]-2'-methyl-4'-(5-methyl-1,2,4-oxadiazol-3-yl)biphenyl-4-carboxamide (E1)

2'-methyl-4'-(5-methyl-1,2,4-oxadiazol-3-yl)biphenyl-4-carboxylic acid (EP 0533 268A1) (106 mg) was heated under reflux in excess thionyl chloride (3 ml) under argon for 1 hr, and the excess thionyl chloride evaporated under reduced pressure. The resulting acid chloride was dissolved in dichloromethane (10 ml) and treated with 5-amino-2,3-dihydrobenzofuran-7-yl)-(2-dimethylaminoethyl)carbamic acid tert-butyl ester (D7) (116 mg) and triethylamine (0.06 ml). The mixture was stirred at room temperature overnight then the solvent was evaporated under reduced pressure. The residue was partitioned between aqueous sodium bicarbonate and chloroform, the organic phase was dried ($Na_2SO_4$) and the solvent evaporated under reduced pressure. The resulting material was dissolved in dichloromethane (20 ml) and stirred with trifluoroacetic acid (4 ml) for 1h at room temperature. The mixture was washed with sodium bicarbonate solution, dried. ($Na_2SO_4$), and the solvent evaporated under reduced pressure, to give a semi-solid which was chromatographed on silica, eluting with methanol and dichloromethane, to give the title compound (24 mg, 13%).

$^1$H NMR (250 MHz, $CDCl_3$)

δ(ppm): 8.01 (s, 1H), 7.99–7.9 (m, 3H), 7.85 (s, 1H), 7.45 (d, 2H), 7.35 (d, 1H), 6.97 (s, 1H), 6.76 (s, 1H), 4.58 (t, 2H), 4.43–4.04 (br s, 1H), 3.3–3.15 (m, 4H), 2.68 (s, 3H), 2.59 (t, 2H), 2.35 (s, 3H), 2.28 (s, 6H)

EXAMPLE 2

N-[7-(2-dimethylamino)ethoxy-2,3-dihydrobenzofuran-5-yl]-2'-methyl-4'-(5-methyl-1,2,4-oxadiazol-3-yl)biphenyl-4-carboxamide 2'-methyl-4'-(5-methyl-1,2,4-oxadiazol-3-yl)biphenyl-4-carboxylic acid (EP 0533 268A1) (166 mg) was heated under reflux with excess thionyl chloride (4 ml) under argon for 1 h and the excess thionyl chloride evaporated under reduced pressure. The resulting acid chloride was dissolved in tetrahydrofuran (15 ml) and treated with 5-amino-7-(2-dimethylamino)ethoxy-2,3-dihydrobenzofuran (D12) (125 mg) in tetrahydrofuran (10 ml) and a solution of sodium hydroxide (45 mg) in water (0.5 ml). The mixture was stirred at room temperature overnight then the solvent was evaporated under reduced pressure. The residue was partititioned between water and dichloromethane, the organic phase was dried ($Na_2SO_4$) and the solvent evaporated under reduced pressure, to give the crude product. This was chromatographed on silica, eluting with methanol and dichloromethane, to give the title compound as an off-white powder. (124 mg, 45%). m.p. 180°–1° C.

$^1$H NMR (250 MHz, $CDCl_3$) δ(ppm): 8.07 (s, 1H), 8.02–7.9 (m, 4H), 7.45 (d, 2H), 7.33 (d, 1H), 7.25 (s, 1H), 7.12 (s, 1H), 4.6 (t, 2H), 4.23 (t, 2H), 3.23 (t, 2H), 2.92 (t, 2H), 2.7 (s, 3H), 2.48 (s, 6H), 2.32 (s, 3H).

EXAMPLE 3

N-[7-(3-Dimethylaminopropyl)-2,3-dihydrobenzofuran-5-yl]-2'-methyl-4'-(5-methyl-1,2,4-oxadiazol-3-yl)biphenyl-4-carboxamide oxalate (E3)

Following the procedure outlined in Example 2, 2'-methyl-4'-(5-methyl-1,2,4-oxadiazol-3-yl)biphenyl-4-carboxylic acid (EP 0533 268A1) (335 mg) and 7-(3-dimethylaminopropyl)-2,3-dihydrobenzofuran-5-ylamine (D18) (250 mg) were converted to the title compound (101 mg, 18%) which was converted to the oxalate salt. Mp 155°–8° C.

$^1$H NMR (250 MHz, $CDCl_3$) (freebase) δ(ppm): 8.05–7.9 (m, 5H), 7.58 (s, 1H), 7.49 (s, 1H), 7.44 (s 1H), 7.35 (d, 1H), 7.1 (s, 1H), 4.58 (t, 2H), 3.22 (t, 2H), 2.68 (s, 3H), 2.6 (t, 2H), 2.51–2.4 (m, 2H), 2.37–2.3 (m, 9H), 1.96–1.8 (m, 2H)

I claim:

1. A compound of formula (I) or a salt thereof:

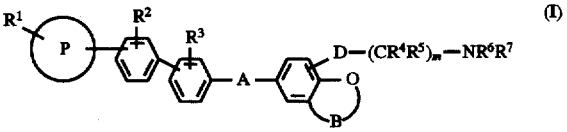

in which

P is 1,2,4-oxadiazole $R^1$, $R^2$ and $R^3$ are independently hydrogen, halogen, $C_{1-6}$alkyl, $C_{3-6}$cycloalkyl, $C_{3-6}$cycloalkenyl, $C_{1-6}$alkoxy, acyl, aryl, acyloxy, hydroxy, nitro, trifluoromethyl, cyano, $CO_2R^8$, $CONR^9R^{10}$, $NR^9R^{10}$ where $R^8$, $R^9$ and $R^{10}$ are independently hydrogen or $C_{1-6}$alkyl;

$R^4$ and $R^5$ are independently hydrogen or $C_{1-6}$alkyl;

$R^6$ and $R^7$ are independently hydrogen or $C_{1-6}$alkyl,

A is CONH or HNCO;

B is —$(CR^{11}R^{12})p$— where $R^{11}$ and $R^{12}$ are independently hydrogen or $C_{1-6}$alkyl and p is 2;

m is 1 to 4; and

D is oxygen, $S(O)_n$ where n is 0, 1 or 2, or D is $NR^{10}$ where $R^{10}$ is hydrogen or $C_{1-6}$alkyl, or D is $CR^4=CR^5$ or $CR^4R^5$ where $R^4$ and $R^5$ are independently hydrogen or $C_{1-6}$alkyl.

2. A compound according to claim 1 in which $R^1$ and $R^2$ are $C_{1-6}$ alkyl.

3. A compound according to claim 1 in which $R^3$ is hydrogen.

4. A compound according to claim 1 in which A is CONH, and D is oxygen, NH or $CH_2$.

5. A compound according to claim 1 in which m is 2 and $R^7$ and $R^6$ are both $C_{1-6}$alkyl.

6. A compound according to claim 1 which is:

N-[7-[(2-dimethylaminoethyl)amino]-2,3-dihydrobenzofuran-5-yl]-2'-methyl4'-(5-methyl-1,2,4-oxadiazol-3-yl)biphenyl-4-carboxamide, N-[7-(2-dimethylamino)ethoxy-2,3-dihydrobenzofuran-5-yl]-2'-methyl-4'-(5-methyl-1,2,4-oxadiazol-3-yl)biphenyl-4-carboxamide, N-[7-(3-Dimethylaminopropyl)-2,3-dihydrobenzofuran-5-yl]-2'-methyl-4'-(5-methyl-1,2,4-oxadiazol-3-yl)biphenyl-4-carboxamide, or a pharmaceutically acceptable salt thereof.

7. A pharmaceutical composition which comprises a compound according to claim 1 in association with a pharmaceutically acceptable carrier or excipient.

8. A compound according to claim 1 wherein $R^6$ and $R^7$ are methyl.

9. A compound according to claim 1 wherein $R^{11}$ and $R^{12}$ are hydrogen.

* * * * *